United States Patent [19]

Vert et al.

[11] Patent Number: 5,662,938

[45] Date of Patent: Sep. 2, 1997

[54] BIORESORBABLE-POLYMER MICROSPHERES OF HYDROXY ACID POLYMER FREE FROM SURFACTANT, THEIR PREPARATION AND THEIR APPLICATION AS A DRUG

[75] Inventors: Michel Vert, Castelnau le Lez; Jean Coudane, Montpellier; Christine Ustariz, Montpellier; Gregoire Schwach, Montpellier, all of France

[73] Assignee: Centre National de la Recherche Scientifique (CNRS), Paris, France

[21] Appl. No.: 347,380

[22] PCT Filed: Jun. 15, 1993

[86] PCT No.: PCT/FR93/00576

§ 371 Date: Jan. 19, 1995

§ 102(e) Date: Jan. 19, 1995

[87] PCT Pub. No.: WO93/25191

PCT Pub. Date: Dec. 23, 1993

[30] Foreign Application Priority Data

Jun. 15, 1992 [FR] France ................................ 92 07186

[51] Int. Cl.$^6$ .................................................. A61K 9/16
[52] U.S. Cl. .......................... 424/501; 424/426; 514/772; 428/402; 264/4.6
[58] Field of Search ...................... 424/501, 426, 424/428; 514/772; 428/402; 264/4.6

[56] References Cited

U.S. PATENT DOCUMENTS

| 4,818,542 | 4/1989 | DeLuca et al. ................ 424/491 |
| 5,180,765 | 1/1993 | Sinclair ........................... 524/306 |

FOREIGN PATENT DOCUMENTS

| 0202065 | 11/1986 | European Pat. Off. . |
| 88/08300 | 11/1988 | WIPO . |
| WO92/16193 | 10/1992 | WIPO . |

OTHER PUBLICATIONS

R. Bodmeier et al., International Journal of Pharmaceutics, 51 (1989) 1–8.

*Primary Examiner*—Edward J. Webman
*Attorney, Agent, or Firm*—Oliff & Berridge

[57] ABSTRACT

Bioresorbable microspheres and a process for making microspheres are provided. The microspheres are made of poly(hydroxy acid) having a bimodal distribution; at least one poly(hydroxy acid) having molecular mass of at least 20,000 and at least one poly(hydroxy acid) having a molecular mass of less than 5,000. The microspheres may contain an active substance for gradual release into a biosystem.

13 Claims, No Drawings

BIORESORBABLE-POLYMER MICROSPHERES OF HYDROXY ACID POLYMER FREE FROM SURFACTANT, THEIR PREPARATION AND THEIR APPLICATION AS A DRUG

The invention relates to novel bioresorbable-polymer microspheres free from surface-active agent, their preparation and their application.

The encapsulation of active substances in polymer matrices, in order to protect these active substances or to release them gradually, is well known.

Various systems are known in particular, these also being known as delayed effect systems, which gradually release pharmacologically active principles of therapeutic value, which are dispersed in a polymer matrix, into the body in which they are implanted. The polymers used may be derived from natural polymers (cellulose or proteins) or may be synthetic polymers.

Among the materials which may be implanted into the body, bioresorbable polymers, that is to say polymers which degrade gradually in the body and the degradation products of which polymers are removed by metabolism or by excretion, are particularly advantageous, especially since they circumvent the need for surgical intervention which is intended to remove the implant after its period of operation. This is the case for polyesters derived from hydroxy acids. These polyesters are also known by abbreviation as poly (hydroxy acid)s.

The bioresorbable sustained-release systems may also be in the form of microspheres which may be administered orally, intramuscularly or intravenously.

The term microsphere is understood here to refer to a solid spherical system the average diameter of which does not exceed a few hundred micrometers (in particular 500 µm), this concept encompassing spheres (sometimes referred to as nanospheres) with an average diameter of less than a micrometer.

The main advantage of the microspheres is that they enable active principles, having a prolonged period of action by virtue of their gradual release, to be administered readily by injection, thereby enhancing the therapeutic action of these active principles and reducing the possible toxicity thereof. This method avoids the installation of implants which may be the source of inflammations or of infections. It also avoids repeated administrations since the active principle exerts its action over a longer period.

Microspheres containing no active principle are also therapeutically useful: they may serve especially to bring about the embolization of angiomas.

Microspheres may be obtained by various techniques, especially according to the so-called solvent evaporation method. This method may be described as follows: the active principle to be encapsulated and the polymer which constitutes the microspheres are dissolved in a water-immiscible volatile organic solvent. The resulting solution is emulsified using a surface-active agent. Gradual evaporation of the organic solvent leads to the conversion of the droplets of the emulsion into solid microspheres in which the active principle is trapped.

This technique thus involves a surface-active agent whose function is to promote the stability of the emulsion and thus to guarantee the correct formation of the microspheres and the stability of the suspensions of the latter in liquid injection media.

However, the presence of a surfactant at the surface of the microspheres, in a body, is liable to modify the characteristics and the performance of the delayed effect system and even to make it unusable if the surfactant is toxic, or if it is strongly bound to the surface, since it modifies the body/synthetic polymer material interface. Indeed, it is this interface which controls the release of the active principle and the response of the implantation medium.

One of the surfactants best adapted to the production of polymer-based microparticles is polyvinyl alcohol (PVA), which gives rise to very little formation of particle agglomerates and which enables microspheres with a size of less than 150 µm to be obtained readily. However, the use of PVA raises potential toxicity problems. The reason for this is that this compound is considered to be potentially carcinogenic, particularly when it is administered parenterally.

Thus, the use of a surfactant of any nature, during the preparation of the microspheres by solvent evaporation, is liable to modify the characteristics of the delayed effect system. The morphology of the microspheres (size, shape, presence of surfactant at the surface) and also the effectiveness of the system both for incorporating the active substance and for releasing it, are influenced by the surfactant.

It has now been discovered that it is possible to obtain microspheres the only constituents of which, besides the encapsulated active substance, are those of the polymer matrix, and which microspheres may be prepared without the need to add conventional surfactants. In addition, the microspheres obtained give stable suspensions.

The invention thus relates to microspheres consisting of a polymer matrix and optionally of at least one active substance encapsulted in the said polymer matrix, which matrix is made of at least one hydroxy acid polymer or copolymer, characterized in that the said microspheres are free from constituents other than the active substance (when it is present) and the constituents of the polymer in other words, the microspheres of the invention contain no surfactant.

It has, indeed, been discovered that it is possible to obtain microspheres exhibiting satisfactory characteristics, without using surfactants, by using mixtures of poly(hydroxy acid)s, of high molecular weight and of low molecular weight, as will be specified below.

The term poly(hydroxy acid) refers here to a polyester the structure of which results from esterification of the hydroxyl group of one hydroxy acid molecule by another hydroxy acid molecule, and so on. Such a polymer is a homopolymer or a copolymer.

The microspheres of the invention may be characterized both by the absence of surface-active agents and by an (at least) bimodal distribution of the molecular masses of the constituents of the polymer matrix.

The microspheres of the invention, the polymer matrix of which consists essentially of at least one hydroxy acid polymer or copolymer, may be prepared by a process in which the said polymer or copolymer is dissolved in a water-immiscible volatile liquid organic phase, an active substance is optionally dissolved or dispersed in the said organic phase, an emulsion of the organic phase obtained is prepared in an aqueous continuous phase, the solvent is evaporated off and, if so desired, the solid microspheres obtained are separated from the aqueous phase, this process being characterized in that the said polymer or copolymer comprises at least one poly(hydroxy acid) with an average molecular mass at least equal to 20,000, and at least one poly(hydroxy acid) with an average molecular mass of less than 5000, in that after production of the emulsion, the pH is adjusted to a value of 6–8 by addition of a base, and in that during the step of evaporating the organic solvent, the pH is adjusted to a value of 6–8 by continuous addition or by repeated additions of a base.

As base, sodium hydroxide or potassium hydroxide or an amine such as triethylamine is used for example.

Obviously, the water may be replaced by any other liquid in which the volatile organic phase is insoluble.

Among the polymers constituting the matrix of the microspheres of the invention, there will be mentioned, for example, poly(alpha-hydroxy acid)s, poly(beta-hydroxy acid)s such as poly(beta-hydroxybutyrate) for example, polymers of monoesterified malic acid, such as poly(benzyl malate) or polymers of other hydroxy acids, such as poly (ε-caprolactone), and the copolymers thereof. Among the preferred polymers, there will more particularly be mentioned the poly(alpha-hydroxy acid)s such as poly(lactic acid) and poly(glycolic acid), and the copolymers thereof. It is known that these polymers are linear polyesters containing repeating units of formula: —[O—CH(R)—CO]—, in which R represents H in the case of poly(glycolic acid) and R represents —$CH_3$ in the case of poly(lactic acid).

It is also possible to use copolymers (polyesters) derived from these hydroxy acids, for example copolymers of the type poly(lactic-co-glycolic acid) which contain repeating units —[O—CH($CH_3$)—CO—]$_p$ and [—O—$CH_2$—CO—]$_q$ p and q being the molar proportions of the lactic and glycolic units respectively.

The polymers used are preferably amorphous, or at least partly amorphous.

The poly(hydroxy acid)s with an average molecular mass at least equal to 20,000, and in particular at least equal to 40,000, are known products or may be prepared according to the known methods. Some of them are, for that matter, commercial products. For example, in order to prepare a poly(lactic acid) of high average molecular mass, or a lactic-glycolic copolymer, it is possible to proceed by ring-opening of cyclic diesters (lactide, glycolide or mixtures thereof) according to the usual methods. In the case of lactic acid, which exists in D and L optically active forms, it is preferable to use a mixture of these two forms containing, for example, an amount of D-lactic units which is sufficient for the polymer obtained to be amorphous. A starting material consisting of a D- and L-lactide mixture which is chosen such that the proportion of D-lactic units is sufficient for the polymer obtained to be amorphous is especially used. This proportion may be readily determined in each case by simple routine experiments. Polymers containing from 30 to 70%, and in particular 50%, of units derived from D-lactic acid will usually be used.

The poly(hydroxy acid)s of low average molecular mass, below 5000, are also known products, some of which are marketed, or may be prepared according to the known methods. For example, in order to prepare a poly(lactic acid) of low average molecular mass, it is possible to proceed by polycondensation of mixtures of L- and D-lactic acids, in particular by polycondensation of D, L-lactic acid. Corresponding copolymers are prepared in a similar manner.

The molecular masses of the polymers used according to the invention may be determined in solution for example, by gel permeation chromatography, by comparison with polymer reference standards, especially polystyrene reference standards.

The molecular masses are number average molecular masses or weight average molecular masses. For example, the lower limit of 20,000, for the polymer of high molecular mass (MM), is a number average MM, and the maximum value of 5000 for the polymer of low MM is a weight average MM.

Polymers whose polymolecularity index is not greater than 3 approximately, and in particular is less than 2, are preferably used.

The organic phase used in the process of the invention mainly comprises an organic solvent which is water-immiscible, or very sparingly soluble in water, such as chloroform, dichloromethane, and the like.

This organic phase contains, in the dissolved state, the polymer of high molecular mass, at least equal to 20,000, and the polymer of low molecular mass, below 5000.

The proportions of polymer of low molecular mass, relative to the polymer of high molecular mass, are the proportions which make it possible to obtain microspheres of sufficient quality (especially a satisfactory state of surface), and having the desired particle sizes (especially sufficiently low), in an acceptable yield. These proportions may be determined in each case by simple routine experiments. In general, it will be possible to use a proportion of from 30 to 300%, and in particular from 50% to 150%, by weight of low molecular mass polymer relative to the weight of high molecular mass polymer. Increasing the proportion of low molecular mass polymer makes it possible to obtain a reduction in the particle size.

The organic phase may additionally contain an active substance, which may be added before or after addition of the polymers; the active substance may especially be chosen from steroid hormones or the synthetic analogous thereof (for example progesterone, norgestrel, estradiol, norethisterone, testosterone, hydrocortisone, prednisolone and dexamethasone), anticancer agents (doxorubicin, bleomycin, cisplatin and 5-fluorouracil), narcotics antagonists (for example Naltrexone), neurosedatives or anaesthetics (phenobarbitone, chlorpromazine, methadone and diazepam), antibiotics (erythromycin and gentamicin), and the like.

The active substance is preferably a lipophilic substance, so as to facilitate its incorporation into the microspheres.

An emulsion is then prepared by gradually pouring, with stirring, the organic phase into an appropriate amount of water. The amount of water may be determined, for example, so that the minimum amount of water is used, in order to limit the diffusion of the active principle (when it is present) into the aqueous phase, it being necessary, however, for the amount of water to be sufficient so that the microspheres are as uniform in shape as possible. The amount of water may thus be determined in each case by simple routine experiments.

When it is desired to obtain nanoparticles, the emulsion may be subjected to the action of ultrasound or of a homogenizer so as to increase the divided state of the emulsion. Ultrasound is applied or homogenization is carried out for a period of time which is sufficient for the microdroplets of the emulsion to reach a predetermined, sufficiently small size. Here also, development of the process may be achieved by simple routine experiments.

After preparation of the emulsion, the pH is adjusted to a value of 6–8, in particular 7–8, by addition of a base such as sodium hydroxide, potassium hydroxide or trimethylamine, since partial dissolution of the polyacids of low molecular mass imparts an acidic pH to the water. It is thus important to adjust the pH to a sufficient value such that the carboxylic groups, in the aqueous phase or in contact with the latter, are in the carboxylate form, which is necessary for the microspheres to be stabilized.

It is not desirable for the aqueous phase to be brought to a pH of 7–8 from the start of the preparation of the emulsion, since it would then be feared that the polymers of low molecular mass would associate to form. micelles in the aqueous phase.

The organic solvent is then evaporated off, at a temperature which may range, for example, from 0° to 40° C. This operation may be facilitated by working under reduced pressure.

During the step of evaporation of the organic solvent, the pH is adjusted to a sufficient value, for example 6–8, in particular 7–8, for the reasons already indicated above, by making continuous addition or by making repeated additions of a base such as those mentioned above.

Obviously, during the evaporation step, the emulsion is kept suitably stirred.

After the step of evaporation of the organic solvent, the microspheres may be collected, for example by centrifugation or filtration. They may then be dried and optionally screened.

The microspheres according to the invention may be used according to the known methods. In particular, when the active substance incorporated is a drug, the microspheres may be used orally, in the form of powders, aqueous suspensions or capsules. When the microspheres are sufficiently small, for example smaller than 150 μm, they may he administered by injection, according to the known methods. In addition, as indicated above, microspheres optionally containing no active substance may be injected so as to bring about a local embolization of the vascularization system of angiomas.

Another subject of the invention is a drug based on microspheres as defined above.

The examples which follow illustrate the invention.

EXAMPLE 1

A) Preparation of the polymers a) A D,L-lactic acid/glycolic acid copolymer, containing 25% of units derived from glycolic acid, was prepared in the following way:

78.83 g of D,L-lactide and 21.17 g of glycolide are mixed together to form 100 g of the polymerizable mixture of monomers. 0.025% by weight of antimony trifluoride is added. The mixture is degassed by repeated cycles of vacuum and nitrogen. After sealing under vacuum, the polymerization is carried out in bulk at 160° C. for 3 days.

The number average molecular mass of the copolymer, determined by gel permeation chromatography, by comparison with polystyrene reference standards, is 38,000. The polymolecularity index (I) is: 1.6.

b) A poly(lactic acid) of low molecular mass was prepared by polycondensation of D,L-lactic acid at 140° C. under vacuum for three days. The reaction product is cooled and dissolved in acetone. Water is added to the solution so as to precipitate the polymer, while the residual monomers remain in solution. The polymer is then dried under vacuum.

Its weight average molecular mass, determined by gel permeation chromatography, is 2500, compared with polystyrene reference standards: I=1.5.

B) Preparation of the microspheres 3.8 g of the copolymer and 1.2 g of poly(lactic acid) are dissolved in 50 ml of dichloromethane.

The solution obtained is gradually poured, with stirring, into 1250 ml of distilled water. The pH, which is initially 5–6, falls rapidly to 3. Approximately one minute after the end of the addition of the organic phase, aqueous 0.2N sodium hydroxide solution is added in order to return the pH to 7.5 approximately. The organic solvent is then evaporated off, by natural volatilization at room temperature for 4 hours, with stirring.

0.2N sodium hydroxide is added periodically during the evaporation phase, with continued stirring, in order to return the pH to above 7. As the dichloromethane evaporates, the pH falls less rapidly and, towards the end of the operation, it stabilizes in the region of 7.

The microspheres obtained are then collected by filtration and are dried under reduced pressure.

5 screens having mesh sizes of 500, 250, 125, 100 and 80 μm respectively are used to study the size distribution of the microspheres. The particles larger than 500 μm in size are removed. The amounts of microspheres recovered in each screen are weighed.

The results are summarized in Table I below:

TABLE I

| Diameter μm | % by weight |
| --- | --- |
| between 250 and 500 | 25.6 |
| between 125 and 250 | 45.2 |
| between 100 and 125 | 16.8 |
| between 80 and 100 | 7.5 |
| <80 | 4.9 |

Under an optical microscope, the microspheres are substantially spherical in shape and have a uniform surface.

The results were confirmed by scanning electron microscopy. The very uniform state of the surface of the microspheres is comparable with that of the microspheres obtained using polyvinyl alcohol as a surface-active agent.

EXAMPLE 2

The process is performed in a similar manner to that described in Example 1, but using equal parts (by weight) of the copolymer and of the poly(lactic acid) of low molecular mass.

Microspheres with a diameter of less than 500 μm are obtained in a yield of 61%. The particles smaller than 45 μm in size are also isolated.

The results are summarized in Table II below:

TABLE II

| Diameter μm | % by weight |
| --- | --- |
| between 250 and 500 | 6.04 |
| between 125 and 250 | 5.56 |
| between 100 and 125 | 7.03 |
| between 80 and 100 | 27.19 |
| between 45 and 80 | 48.50 |
| <45 | 5.68 |

EXAMPLE 3

1 g of copolymer obtained in Example 1 (A,a) and 1 g of the poly(lactic acid) of low molecular mass obtained in Example 1 (A,b) and also 0.25 g of progesterone are dissolved in 20 ml of dichloromethane.

The solution obtained is gradually poured, with stirring, into 500 ml of distilled water. The pH falls rapidly to 3. Approximately one minute after the end of the addition of the organic phase, the pH is returned to 7.5 by addition of 0.2N sodium hydroxide. The process is then performed as described in Example 1.

Microspheres are obtained in which the progesterone is incorporated.

We claim:

1. Microspheres consisting of a composition selected from the group consisting of (a), a polymer matrix and (b) a polymer matrix and at least one active substance encapsulated in the said polymer matrix, said matrix being made of a plurality of hydroxy acid polymer or copolymer, said plurality of polymer or copolymer having a bimodal distribution of molecular masses wherein a first of said plurality of polymer or copolymer has a molecular mass at least equal to 20,000 and a second of said plurality of polymer or copolymer has a molecular mass of less than 5000.

2. Microspheres according to claim 1, characterized in that they are smaller than 500 μm in size.

3. Drug based on microspheres as defined in claim 1.

4. Microspheres according to claim 1, wherein said first of said plurality of polymer or copolymer has a molecular mass of greater than 40,000.

5. Process for the preparation of microspheres consisting of a composition selected from the group consisting of (a) a polymer matrix and (b) a polymer matrix and at least one active substance encapsulated in the said polymer matrix, said matrix being made of a plurality of hydroxy acid polymer or copolymer, said plurality of polymer or copolymer having a bimodal distribution of molecular masses wherein a first of said plurality of polymer or copolymer has a molecular mass at least equal to 20,000 and a second of said plurality of polymer or copolymer has a molecular mass of less than 5000, said process comprising:

obtaining a mixture according to at least one step selected from the group consisting of (a) dissolving said plurality of polymer or copolymer in a water immiscible volatile liquid organic phase and (b) dissolving said plurality of polymer or copolymer in a water-immiscible volatile liquid organic phase, and dissolving or dispersing an active substance in said organic phase;

preparing an emulsion comprising said mixture dispersed in an aqueous continuous phase; said emulsion being free from added surfactant; and evaporating said organic phase off;

wherein said polymer or copolymer has a bimodal distribution, said polymer or copolymer comprising at least one poly(hydroxy acid) with an average molecular mass at least equal to 20,000, and at least one poly(hydroxy acid) with an average molecular mass of less than 5,000, wherein, after production of the emulsion, the pH is adjusted to a value of 6–8 by addition of a base, and wherein during the step of evaporating the organic solvent, the pH is adjusted to a value of 6–8 by addition of a base.

6. Process according to claim 5, characterized in that the poly(hydroxy acid) with an average molecular mass at least equal to 20,000 is chosen from polymers and copolymers of alpha-hydroxy acids.

7. Process according to claim 6, characterized in that the said poly(alpha-hydroxy acid)s are chosen from poly(lactic acid)s and poly(glycolic acid)s.

8. Process according to claim 5, characterized in that the proportion of polymer of low molecular mass, relative to the polymer of high molecular mass, is sufficient to obtain microspheres having desired sufficiently low particle sizes.

9. Process according to claim 8, characterized in that the said proportion may range from 30 to 300% by weight, and in particular from 50 to 150% by weight.

10. Process according to claim 9, wherein said proportion may range from 50 to 150% by weight.

11. Process according to claim 5, wherein said microspheres are solid microspheres and said process further comprises separating said solid microspheres from the aqueous phase.

12. Process according to claim 5, wherein said addition of a base is continuous.

13. Process according to claim 5, wherein said addition of a base comprises repeated additions of a base.

* * * * *